United States Patent [19]

Fleming

[11] Patent Number: Plant 7,426

[45] Date of Patent: Jan. 22, 1991

[54] KALANCHOE PLANT NAMED RADIANCE

[75] Inventor: Margaret M. Fleming, Soquel, Calif.

[73] Assignee: The Plant Company, Soquel, Calif.

[21] Appl. No.: 422,087

[22] Filed: Oct. 16, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Kalanchoe plant named Radiance particularly characterized by its red flower color; flower diameter of 13 to 14 mm at maturity; flowering response of from 9 weeks in summer to 11 weeks in winter after start of short days; good keeping quality of flowers and foliage; branches freely with or without pinching; compact plant habit; attractive, small dark green foliage; responds well to B-9 applications to reduce internode length and peduncle elongation; and adaptability to pot sizes from 10 to 15 cm.

2 Drawing Sheets

The present invention relates to a new and distinctive cultivar of Kalanchoe plant, botanically known as *Kalanchoe blossfeldiana* Poelln., and referred to by the cultivar name Radiance.

Radiance, identified as 406-232, is a product of a planned breeding program which had the objective of creating new Kalanchoe cultivars for year-round commercial production, with earlier flowering response, good branching yet compact flowering habit, suitable for flowering in pots ranging from 10 to 15 cm, and with good flower and foliage keeping quality.

Radiance was originated from a cross by the inventor Margaret M. Fleming in a controlled breeding program in Half Moon Bay, Calif., in 1983.

The female parent of Radiance was the cultivar Eternity, disclosed in U.S. Plant Pat. No. 5,253. The male parent was the cultivar Cinnabar, disclosed in U.S. Plant Pat. No. 5,160.

Radiance was discovered and selected by the inventor as one flowering plant within the progeny of the stated cross in September, 1984 in a controlled environment in Half Moon Bay, Calif.

The first act of asexual reproduction of Radiance was accomplished when vegetative cuttings were taken by the inventor from the initial selection in January, 1985 in a controlled environment in Half Moon Bay, Calif.

Horticultural examination of controlled flowerings of successive plantings has shown that the unique combination of characteristics as herein disclosed for Radiance are firmly fixed and are retained through successive generations of asexual reproduction. Radiance has not been observed under all possible environmental conditions. The phenotype may vary significantly with variations in environment such as temperature, light intensity and daylength.

The following observations, measurements and comparisons describe plants grown in Soquel, Calif., under greenhouse conditions which approximate those generally used in commercial greenhouse practice.

The following traits have been repeatedly observed and are determined to be basic characteristics of Radiance, which, in combination, distinguish this Kalanchoe as a new and distinct cultivar:

1. Red flower color.
2. Flower diameter of 13 to 14 mm at maturity.
3. Flowering response of from 9 weeks in summer to 11 weeks in winter.

4. Good keeping quality of flowers and foliage.
5. Branches freely with or without pinching.
6. Compact plant habit.
7. Attractive small dark green foliage, which together with foliage size, form and durability, result in foliage having superior characteristics.
8. Responds well to B-9 to reduce internode length and peduncle elongation.
9. Proper scheduling makes this new cultivar suitable for production in 10 cm to 15 cm pots.

The accompanying photographic drawings show typical inflorescence and leaf characteristics of Radiance, with colors being as nearly true as possible with illustrations of this type. Sheet 1 is a color photograph of Radiance grown as a non-pinched flowering Kalanchoe in a 10 cm pot. Sheet 2 is a black and white photograph showing the leaves of Radiance at three stages of development (mature, intermediate and immature).

Of the commercial cultivars known to the inventor, the most similar in comparison to Radiance is the male parent Cinnabar. Similar traits are flowering response, free branching habit, compact plant habit, responsiveness to B-9, and adaptability to various pot sizes. Dissimilarities are that Radiance has a red flower color, compared to the orange-red flower color of Cinnabar, and Radiance has a slightly smaller flower diameter, smaller foliage, and better keeping quality of flowers and foliage than Cinnabar.

Radiance can also be compared with the female parent Eternity. Radiance is similar to Eternity in flower form, durability of foliage, and resistance or immunity to flower and foliar diseases. Radiance differs from Eternity in Radiance's smaller flowers, shorter and narrower leaves which are a darker green in color, more vigorous habit, different leaf serrations, a brighter red flower color with less orange tones, and a much earlier (by at least three weeks) blooming cycle than Eternity. Radiance is one of the earliest blooming varieties, while Eternity is one of the latest.

The cultivar Big Surprise is a sister seedling of Radiance, resulting from the same cross. Similar characteristics are early blooming, long keeping qualities, and relatively small foliage. However, there are distinct differences in the form, color and size of the foliage of each. Perhaps the biggest distinction is plant size. Radiance is much more compact than Big Surprise, with the height of Radiance being in the 13–18 cm. range (above a 10 cm. pot), as compared with the height of 20–30 cm. for Big Surprise when grown under the same conditions.

In the following description color references are made to The Royal Horticultural Society Colour Chart. The color values were determined on plant material grown as a non-pinched pot plant in a 10 cm pot in Soquel, Calif., on Aug. 9, 1988.

Classification:

*Botanical.*—*Kalanchoe blossfeldiana* Poelln. cv. Radiance

*Commercial.*—Flowering pot kalanchoe.

Parentage:

*Female parent.*—Eternity (U.S. Plant Pat. No. 5,253).

*Male parent.*—Cinnabar (U.S. Plant Pat. No. 5,160).

Propagation:

(A) *Type cutting.*—Short tip cutting, with stems up to 2 cm.

(B) *Time to root.*—10 days at 21° C. in summer, 14 days at 21° C. in winter.

(C) *Rooting habit.*—Many very fine roots, fibrous.

Plant description:

(A) *Form.*—Intermediate, compact, upright growth. Growing and scheduling practices can produce a small plant in a 10 cm pot up to a larger plant in a 15 cm pot.

(B) *Habit of growth.*—Rate of growth moderate for this type of plant. Generally, shoots are formed at every node; Internode length of natural vegetative plant, 12–25 mm.

(C) *Height.*—Short to medium, 13–18 cm. above a 10 cm. pot, with 1–3 applications of 3500 ppm B-9 SP linear growth regulator.

(D) *Foliage description.*—Leaves simple, opposite, slightly lobed. 1. Size: Relatively small; average full grown leaf in a 10 cm flowering pot is 115 mm long×70 mm wide. 2. Shape: Ovate to elliptic, apex obtuse, base attenuate. 3. Texture: Glabrous, coriaceous, succulent. 4. Margin: Sinuate to crenate. 5. Color: Mature foliage: Upper surface 147A. Under surface 147B. Under certain conditions margins of tips of mature foliage are tinged with 183A to 183C. Apical section of underside of mature foliage is tinged and streaked with 183A to 183C. 6. Durabilty: Superior; no degradation observed even on the lower foliage of plants retained for months beyond normal expectancy.

Flowering description:

(A) *Flowering habit.*—Inflorescence of each shoot is formed by dichotomous branching, starting with opening of terminal flower of main axis, followed by terminal flowers of the side branches, continuing with subsequent development of branches in the inflorescence. Opening of new buds (10–15 mm. in length) will continue for two months or more. Individual flowers last two weeks or more after opening.

(B) *Flowering response.*—Flowering time under controlled daylength after start of short days is 9 weeks in summer to 11 weeks in winter.

(C) *Flowers borne.*—Compound dichasial cymes; peduncle length is 5–10 cm. in length and 3–7 mm. in diameter, depending on growing conditions and application of growth regulator; pedicels 5–7 mm. in length and slightly greater than 1 mm. in diameter.

(D) *Quantity of flowers.*—Very floriferous, on both main axis and side laterals; typical floret count of 80–100 per major inflorescence and 400–500 total per plant in a 10 cm. pot grown in accordance with commercial culture practices; 4 to 6 side laterals in a 10 cm pot.

(E) *Petals.*—1. Shape: Slightly pointed to almost round. 2. Color: Upper surface: Closest to 43B, maturing to 50A. Under surface: Closest to 38C, streaked with 43B. 3. Number of petals: 4, united in corolla. 4. Flower diameter: 13 to 14 mm at maturity.

(F) *Reproductive organs.*—1. Stamens: 8 in number. a. Anther shape: Flat, elliptical, color yellow. b. Filament color: Light green. c. Pollen color: Yellow. 2. Pistils a. Stigma shape: Flat, crystalline, color greenish white. b. Style color: Light green. c. Ovaries: 4-celled, color light green.

(G) *Keeping quality.*—Excellent, particularly for an early blooming variety; flowers last up to two weeks, with the plant being in flower two months or more.

Disease resistance: Radiance is resistant or immune to the foliar disease Powdery Mildew and no occurrences of chlorosis, necrotic spot, tip die-back, root rot, or stem rot have been observed. Radiance is also resistant or immune to the flower disease Botrytis, and no fading or color breaking has been observed.

Fragrance: None perceived in flowers or foliage.

I claim:

1. A new and distinct plant of Kalanchoe named Radiance, as described and illustrated.

* * * * *

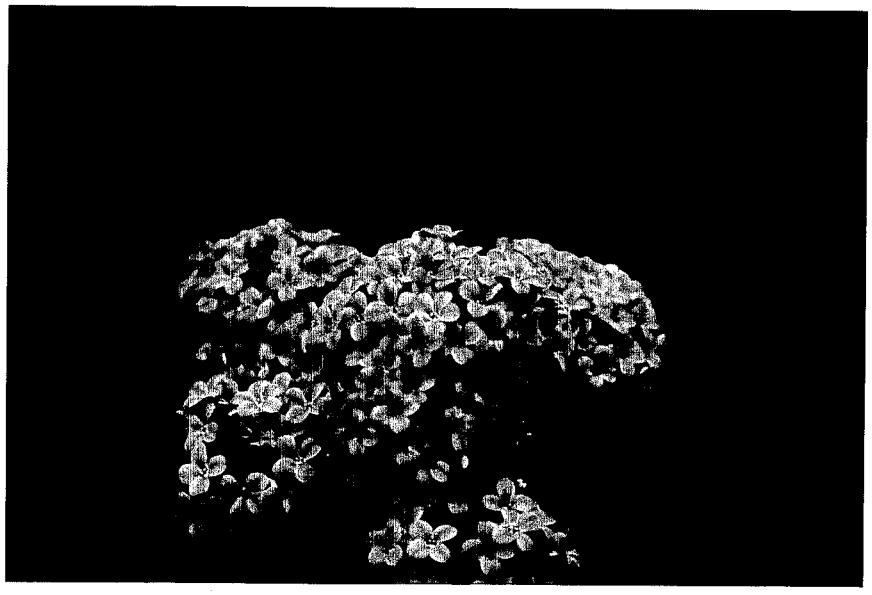

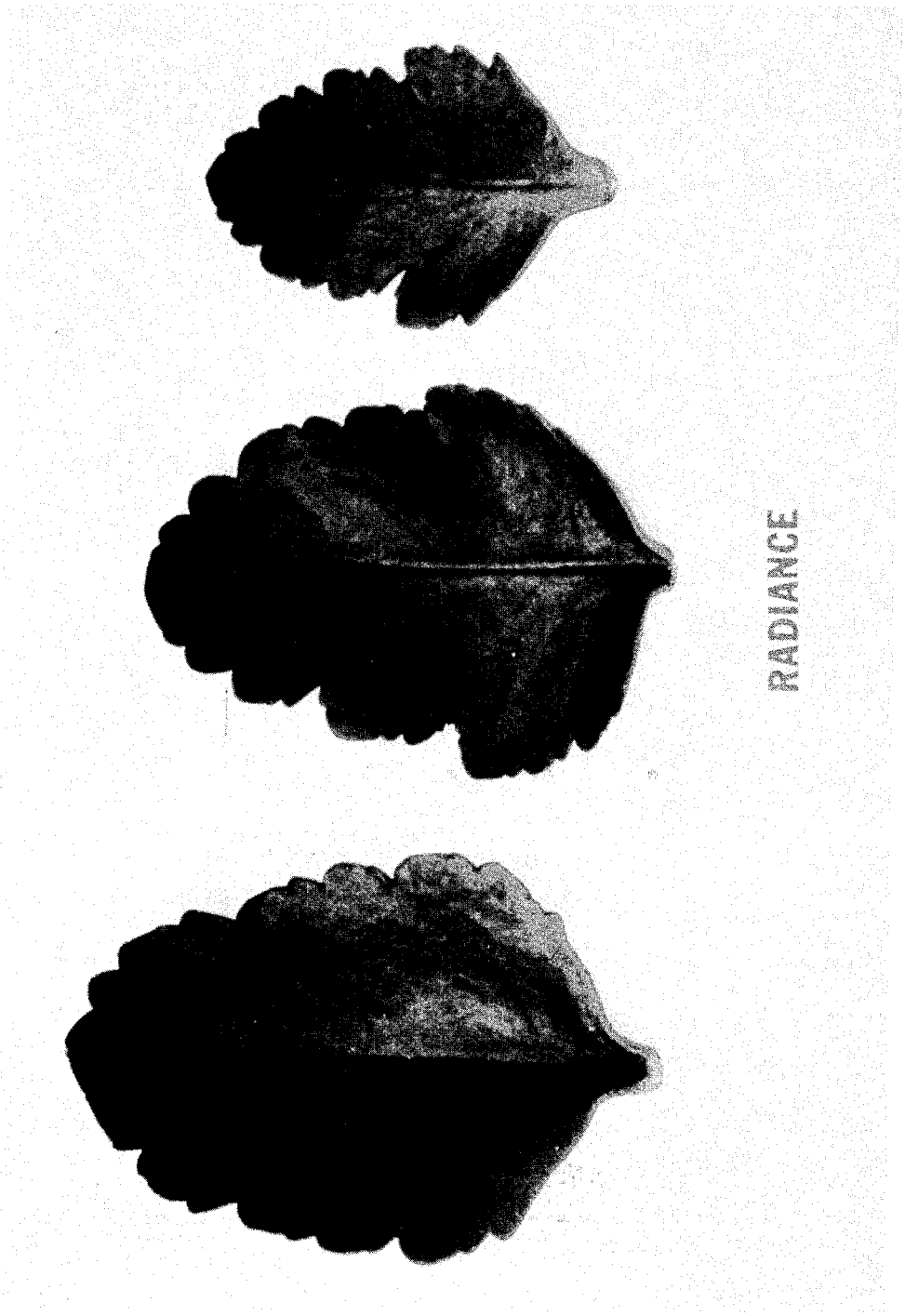
RADIANCE